United States Patent
Xu et al.

(10) Patent No.: US 8,853,393 B2
(45) Date of Patent: Oct. 7, 2014

(54) INTERMEDIATE FOR PREPARING TAPENTADOL OR ANALOGUES THEREOF

(75) Inventors: Ziao Xu, Anhui (CN); Yuanhai Zhao, Anhui (CN); Degang Li, Anhui (CN); Xiaoxiang Li, Anhui (CN)

(73) Assignee: Anhui New Star Pharmaceutical Development Co., Ltd., Hefei, Anhui (CN)

( * ) Notice: Subject to any disclaimer, the term of this patent is extended or adjusted under 35 U.S.C. 154(b) by 0 days.

(21) Appl. No.: 13/884,810

(22) PCT Filed: Jul. 29, 2011

(86) PCT No.: PCT/CN2011/001248
§ 371 (c)(1),
(2), (4) Date: May 10, 2013

(87) PCT Pub. No.: WO2013/016840
PCT Pub. Date: Feb. 7, 2013

(65) Prior Publication Data
US 2013/0231478 A1    Sep. 5, 2013

(51) Int. Cl.
| | | |
|---|---|---|
| C07D 265/30 | (2006.01) | |
| C07D 211/02 | (2006.01) | |
| C07D 295/023 | (2006.01) | |
| C07C 331/28 | (2006.01) | |
| C07C 69/76 | (2006.01) | |
| C07C 51/58 | (2006.01) | |
| C07C 327/00 | (2006.01) | |
| C07C 209/00 | (2006.01) | |
| C07C 233/11 | (2006.01) | |
| C07D 211/16 | (2006.01) | |
| C07C 69/732 | (2006.01) | |
| C07C 213/00 | (2006.01) | |
| C07D 295/192 | (2006.01) | |
| C07C 327/44 | (2006.01) | |
| C07C 59/48 | (2006.01) | |
| C07C 255/37 | (2006.01) | |
| C07C 213/10 | (2006.01) | |
| C07C 51/60 | (2006.01) | |
| C07C 255/36 | (2006.01) | |
| C07C 213/02 | (2006.01) | |
| C07C 67/08 | (2006.01) | |
| C07C 59/64 | (2006.01) | |
| C07C 235/34 | (2006.01) | |
| C07C 327/22 | (2006.01) | |
| C07C 237/20 | (2006.01) | |
| C07C 51/367 | (2006.01) | |
| C07C 41/26 | (2006.01) | |
| C07C 327/28 | (2006.01) | |
| C07D 295/185 | (2006.01) | |
| C07C 41/22 | (2006.01) | |
| C07C 69/734 | (2006.01) | |
| C07C 231/02 | (2006.01) | |
| C07C 253/14 | (2006.01) | |

(52) U.S. Cl.
CPC ......... *C07D 295/192* (2013.01); *C07C 233/11* (2013.01); *C07D 211/16* (2013.01); *C07C 69/732* (2013.01); *C07C 213/00* (2013.01); *C07C 327/44* (2013.01); *C07C 59/48* (2013.01); *C07C 255/37* (2013.01); *C07C 213/10* (2013.01); *C07C 51/60* (2013.01); *C07C 255/36* (2013.01); *C07C 213/02* (2013.01); *C07C 67/08* (2013.01); *C07C 59/64* (2013.01); *C07C 235/34* (2013.01); *C07C 327/22* (2013.01); *C07C 237/20* (2013.01); *C07C 51/367* (2013.01); *C07C 41/26* (2013.01); *C07C 327/28* (2013.01); *C07D 295/185* (2013.01); *C07C 41/22* (2013.01); *C07C 69/734* (2013.01); *C07C 231/02* (2013.01); *C07C 253/14* (2013.01)
USPC ........... 544/176; 546/245; 548/540; 558/230; 558/344; 558/410; 560/75; 562/840; 562/862; 564/74; 564/142; 564/163; 564/170; 564/182; 564/375

(58) Field of Classification Search
USPC ........... 544/176; 546/245; 548/540; 558/230, 558/344, 410; 560/75; 562/840, 862; 564/74, 142, 163, 170, 182, 375
See application file for complete search history.

(56) References Cited

U.S. PATENT DOCUMENTS 6,479,518 B2 * 11/2002 Finke et al. ............... 514/330

*Primary Examiner* — Samantha Shterengarts
(74) *Attorney, Agent, or Firm* — Tianhua Gu; Global IP Services

(57) ABSTRACT

The invention discloses a novel intermediate for preparing tapentadol and analogues thereof, wherein the structural formula is shown as formula I or II, and the groups are defined as the specification. The invention further discloses a method for preparing the novel intermediate and use of the intermediate for preparing tapentadol and analogues thereof. The invention can remarkably improve the product yield and quality of tapentadol, reduce the production cost, and simplify the production procedure. The preparation process is environment friendly, thus more suitable for the requirements of industrial production.

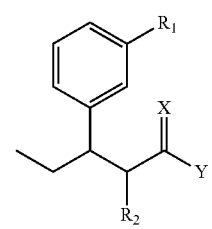

I

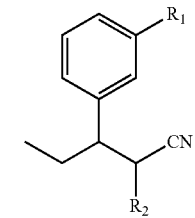

II

6 Claims, No Drawings

INTERMEDIATE FOR PREPARING TAPENTADOL OR ANALOGUES THEREOF

FIELD OF THE INVENTION

The invention belongs to the field of pharmaceutical preparation, and relates to a novel intermediate for preparing tapentadol and analogues thereof.

BACKGROUND OF THE INVENTION

Tapentadol hydrochloride is the hydrochloride of tapentadol, and a novel central analgesic with dual mechanism of action developed by Johnson & Johnson Inc. in USA. It is used as medicine in the form of single isomer of (1R,2R), molecular formula: $C_{14}H_{24}ClNO$, chemical name: (1R,2R)-3-(3-dimethylamino-1-ethyl-2-methylpropyl)-phenol hydrochloride. The structural formula is as follows:

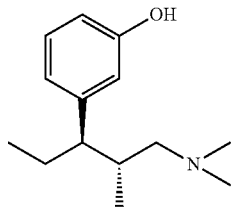 [SMILES: CC[C@@H](c1cccc(O)c1)[C@@H](C)CN(C)C]

Tapentadol belongs to the 1-phenyl-3-(dimethylamine) propane compound which has various pharmacological activities, and can be used for relieving pain (EP963475), also for treating psychosis (DE102007012165), depression (DE10233048), urinary incontinence (WO2002043715), etc.

Tapentadol hydrochloride was on the market under the approval of U.S. Food and Drug Administration on Nov. 21, 2008, and the clinic showed that it has good analgesic effect. Tapentadol hydrochloride is not only a μ opiate receptor agonist, but a norepinephrine reuptake inhibitor (Tzschentke T M, et al., J. Pharm. Exper. Therap., 2007, 323, 265), with the analgesic effect on various animal subjects suffering from acute, inflammatory and chronic neuropathic pains. Its effect is between morphine and tramadol, and the satisfied plasma drug concentration can be reached by intravenous injection or oral administration. It has good tolerance, and is difficult to produce analgesic tolerance and physical dependence compared with morphine. The side effect (especially the gastrointestinal side effect) is further improved compared with the strong opioids of the equivalent analgesic dosage, so the prospect in the treatment of acute and chronic moderate to severe pains is better and better.

The chemical structures of tapentadol and analogues thereof have been disclosed in EP-A-0,693,475 where the prepared precursor of tapentadol, (2R,3R)-3-(3-methoxyphenyl)-N,N,2-trimethylamylamine, is obtained by continuously converting (2R,3R)-1-(dimethylamino)-3-(3-methoxyphenyl)-2-methyl-3-pentanol into the relevant halide by thionyl chloride, removing the tertiary hydroxyl on (2R,3R)-1-(dimethylamino)-3-(3-methoxyphenyl)-2-methyl-3-pentanol, and removing chlorine by zinc borohydride, zinc cyanoborohydride and/or tin cyanoborohydride. The defect of this process is that the halide is obtained by the excessive strong chloridizing agent, thionyl chloride. And, from the point of view of fire and health, it is too hazardous by using the hydriding reagent, such as zinc borohydride, zinc cyanoborohydride and tin cyanoborohydride, in the industrial scale.

Tapentadol is obtained by converting (2S,3S)-1-(dimethylamino)-3-(3-methoxyphenyl)-2-methyl-3-pentanol into the mixture of (2R,3R) and (2R,3S)-3-(3-methoxy-phenyl)-N,N,2-trimethylpentylamine by the prepared precursors in WO-2004/108658 and WO-2005/00078. The two replacement methods are characterized in that the obtained 3-(3-methoxy-phenyl)-N,N,2-trimethylpentylamine is the mixture of (2R,3R) and (2R,3S) stereoisomers and must be separated to obtain the required (2R,3R) stereoisomer.

Based on EP-A-0,693,475, the improvement has been made in CN200780028472.6 where (2R,3R)-1-(dimethylamino)-3-(3-methoxyphenyl)-2-methyl-3-pentanol is subject to hydrogenolysis by a palladium catalyst. This reaction is carried out under the condition of high temperature catalysis, so the reaction condition is very rigour and the requirement on reaction equipment is higher, resulting in inconvenience for the actual production.

SUMMARY OF THE INVENTION

To overcome the shortcomings of the current methods for preparing tapentadol above, the invention provides a novel method for preparing tapentadol and analogues thereof, and a novel intermediate compound for preparing tapentadol and analogues thereof and a preparation method of the intermediate. Tapentadol or salts and analogues thereof can be obtained by preparation through the novel intermediate easily. The implementation of the invention can remarkably improve the product yield of tapentadol (total yield: 12.3%) and product quality (chemical purity >99.5% (HPLC), optical ee %>99%), greatly reduce the production cost, and simplify the production procedure (the multi-step product can be used for the next reaction directly without refinement). The preparation process is environment friendly (all the reagents used for the reactions comply with the requirements of Guideline for Residual Solvents: ICH), thus more suitable for the requirements of industrial production (reaction condition mild and no special equipment required).

The first objective of the invention is to provide a novel intermediate compound for preparing tapentadol and analogues thereof.

A compound shown as formula I or II has the following structural formula:

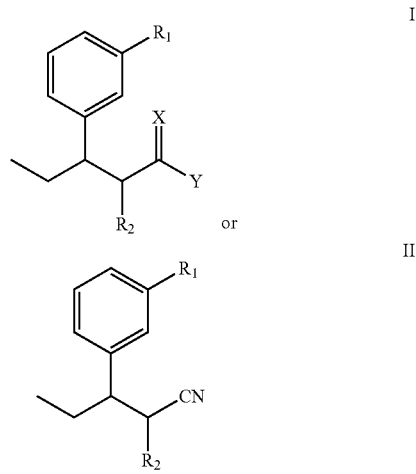

where $R_1$ is selected from halogen, hydroxy, amino, nitrite, nitro, acyl, substituted or unsubstituted alkyl, substituted or unsubstituted cycloalkyl, substituted or unsubstituted alkoxyl, substituted or unsubstituted aryl, substituted or unsubstituted aralkyl, substituted or unsubstituted heteroaryl, substituted or unsubstituted heteroaralkyl, acyloxy, oxyacyl and sulfonyl;

X is selected from oxygen or sulfur;

Y is selected from halogen, $OR_2$ or $NR_3R_4$;

$R_2$ is selected from substituted or unsubstituted alkyl, substituted or unsubstituted cycloalkyl, substituted or unsubstituted aryl, substituted or unsubstituted aralkyl, substituted or unsubstituted heteroaryl, and substituted or unsubstituted heteroaralkyl; and $R_3$ and $R_4$ are separately selected from hydrogen, substituted or unsubstituted alkyl, substituted or unsubstituted cycloalkyl, substituted or unsubstituted aryl, substituted or unsubstituted aralkyl, substituted or unsubstituted heteroaryl, and substituted or unsubstituted heteroaralkyl; or $R_3$, $R_4$ and N form saturated or unsaturated heterocyclyl jointly.

The substituted in the invention refers to that the position capable of being substituted on the group may be substituted by any suitable normal groups, with no special limit.

The alkyl in the invention is preferably selected from straight or branched alkyl containing 1 to 6 carbon atoms.

The alkoxyl in the invention is preferably selected from straight or branched alkoxyl containing 1 to 6 carbon atoms.

The cycloalkyl in the invention is preferably selected from monocyclic saturated carbon ring group containing 3 to 7 carbon atoms.

The aryl in the invention is preferably selected from unsaturated carbon ring group containing 5 to 12 carbon atoms.

The heteroaryl in the invention is preferably selected from unsaturated cyclic group containing 5 to 12 carbon atoms and 1 to 3 oxygen, nitrogen or sulfur atoms.

The aralkyl and heteroaralkyl in the invention are preferably selected from the combinations of the groups above.

The acyl in the invention refers to the group containing —C(=O).

The acyloxy in the invention refers to the group containing —C(=O)O.

The oxyacyl in the invention refers to the group containing —OC(=O).

The sulfonyl in the invention refers to the group containing —(=O)S(=O).

$R_1$ is selected from F, Cl, Br, $CHF_2$, $CF_3$, OH, $SO_2CH_3$, $NH_2$, CN, CHO, —$C_{1-6}$ alkyl, —$C_{1-6}$ alkoxyl, —$C_{3-7}$ cycloalkyl, —$C_{1-3}$ alkylenephenyl, —$C_{1-3}$ alkylenenaphthyl, tetrahydrofuran or —C(=O)$C_{1-6}$ alkyl.

$R_1$ is further preferably selected from Cl, methyl, ethyl, propyl, isopropyl, n-butyl, isobutyl, n-pentyl, methoxy, propoxyl, ethoxyl, isopropoxyl, cyclopropyl, cyclobutyl, cyclopentyl, cyclohexyl, cycloheptyl, OH, or $NH_2$. $R_1$ is most preferably selected from Cl, methyl, OH, NH2 or methoxy.

When Y is selected from $OR_2$, $R_2$ is preferably selected from the saturated alkyl containing 1 to 3 atoms and further preferably selected from methyl, ethyl, propyl or isopropyl.

When Y is selected from $NR_3R_4$, preferably, $R_3$ and $R_4$ are separately selected from hydrogen, substituted or unsubstituted saturated alkyl; or $R_3$, $R_4$ and N form substituted or unsubstituted saturated nitrogen-containing heterocyclyl containing oxygen or not jointly.

When Y is selected from $NR_3R_4$, furthermore, $R_3$ and $R_4$ are preferably and separately selected from hydrogen, methyl, ethyl, propyl or isopropyl; or $R_3$, $R_4$ and N form tetrahydropyrrole ring, piperidine ring, 4-methylpiperidine ring, morpholine ring, methylpiperazine ring or 4-hydroxypiperidine jointly; and $R_3$ and $R_4$ are preferably selected from methyl, ethyl, propyl or isopropyl at the same time.

The compounds in the invention are preferably selected from the following compounds:

| Number | Name | Structural Formula |
|---|---|---|
| 1 | valeryl 2-methyl-3-(3-methoxyphenyl) chloride | |
| 2 | methyl 2-methyl-3-(3-methoxyphenyl) valerate | |
| 3 | methyl 2-methyl-3-(3-methoxyphenyl) sulfovalerate | |
| 4 | methyl 2-methyl-3-(3-hydroxyphenyl) valerate | |
| 5 | methyl 2-methyl-3-(3-hydroxyphenyl) valerate | |
| 6 | 2-methyl-3-(3-hydroxyphenyl) sulfovaleramide | |

| Number | Name | Structural Formula |
|---|---|---|
| 7 | N,N-dimethyl-2-methyl-3-(3-methoxyphenyl)valeramide | |
| 8 | N,N-dimethyl-2-methyl-3-(3-methoxyphenyl)sulfovaleramide | |
| 9 | N,N-dimethyl-2-methyl-3-(3-hydroxyphenyl)valeramide | |
| 10 | N,N-dimethyl-2-methyl-3-(3-hydroxyphenyl)sulfovaleramide | |
| 11 | N,N-diethyl-2-methyl-3-(3-methoxyphenyl)valeramide | |
| 12 | N,N-dipropyl-2-methyl-3-(3-methoxyphenyl)valeramide | |
| 13 | N,N-isopropyl-2-methyl-3-(3-methoxyphenyl)valeramide | |
| 14 | 3-(3-methoxyphenyl)-2-methyl-1-(piperidin-1-yl)pentan-1-one | |
| 15 | 3-(3-methoxyphenyl)-2-methyl-1-(4-methylpiperidin-1-yl)pentan-1-one | |
| 16 | 3-(3-methoxyphenyl)-2-methyl-1-(morpholin-1-yl)pentan-1-one | |
| 17 | 3-(3-methoxyphenyl)-2-methyl-1-(pyrrolidin-1-yl)pentan-1-one | |
| 18 | N,N-dimethyl-2-methyl-3-(3-chlorophenyl)valeramide | |
| 19 | N,N-diethyl-2-methyl-3-(3-chlorophenyl)valeramide | |
| 20 | N,N-dipropyl-2-methyl-3-(3-chlorophenyl)valeramide | |

| Number | Name | Structural Formula |
|---|---|---|
| 21 | N,N-isopropyl-2-methyl-3-(3-chlorophenyl)valeramide | |
| 22 | 3-(3-chlorophenyl)-2-methyl-1-(piperidin-1-yl)pentan-1-one | |
| 23 | 3-(3-chlorophenyl)-2-methyl-1-(4-methylpiperidin-1-yl)pentan-1-one | |
| 24 | 3-(3-chlorophenyl)-2-methyl-1-(morpholin-1-yl)pentan-1-one | |
| 25 | 3-(3-chlorophenyl)-2-methyl-1-(pyrrolidin-1-yl)pentan-1-one | |
| 26 | N,N-dimethyl-2-methyl-3-(3-methylphenyl)valeramide | |
| 27 | N,N-diethyl-2-methyl-3-(3-methylphenyl)valeramide | |
| 28 | N,N-dipropyl-2-methyl-3-(3-methylphenyl)valeramide | |
| 29 | N,N-isopropyl-2-methyl-3-(3-methylphenyl)valeramide | |
| 30 | 3-(3-methylphenyl)-2-methyl-1-(piperidin-1-yl)pentan-1-one | |
| 31 | 3-(3-methylphenyl)-2-methyl-1-(4-methylpiperidin-1-yl)pentan-1-one | |
| 32 | 3-(3-methylphenyl)-2-methyl-1-(morpholin-1-yl)pentan-1-one | |
| 33 | 3-(3-methylphenyl)-2-methyl-1-(pyrrolidin-1-yl)pentan-1-one | |
| 34 | N,N-dimethyl-2-methyl-3-(3-aminophenyl)valeramide | |

-continued

| Number | Name | Structural Formula |
|---|---|---|
| 35 | N,N-diethyl-2-methyl-3-(3-aminophenyl)valeramide | |
| 36 | N,N-dipropyl-2-methyl-3-(3-aminophenyl)valeramide | |
| 37 | N,N-isopropyl-2-methyl-3-(3-aminophenyl)valeramide | |
| 38 | 3-(3-aminophenyl)-2-methyl-1-(piperidin-1-yl)pentan-1-one | |
| 39 | 3-(3-aminophenyl)-2-methyl-1-(4-methylpiperidin-1-yl)pentan-1-one | |
| 40 | 3-(3-aminophenyl)-2-methyl-1-(morpholin-1-yl)pentan-1-one | |

-continued

| Number | Name | Structural Formula |
|---|---|---|
| 41 | 3-(3-aminophenyl)-2-methyl-1-(pyrrolidin-1-yl)pentan-1-one | |
| 42 | 2-methyl-3-(3-hydroxyphenyl)pentanenitrile | |
| 43 | 2-methyl-3-(3-methoxyphenyl)pentanenitrile | |

The compounds in the invention as the intermediate are used for preparing tapentadol and analogues thereof. The compounds in the invention preferably form tapentadol and analogues thereof after the salt is obtained by asymmetric preparation or chiral separation.

The methods for preparing the compound of formula I in the invention are explained hereinafter, and are not intended to limit the composition of the invention.

The compound of formula I in the invention can be prepared by the following methods, however, the conditions of the methods below, such as reactor, solvent, acid, alkali, reaction temperature and time, are not limited to the explanations below. The compounds in the invention can be conveniently prepared by combining various preparation methods in the specification or known in the field, so those skilled in the art of the invention can easily implement such combinations.

The compounds above are prepared by the following methods in the invention.

Method 1 is shown as Scheme 1:

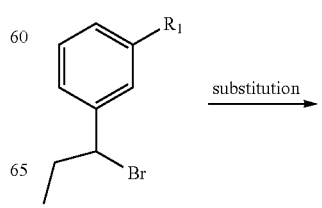

substitution

11

-continued

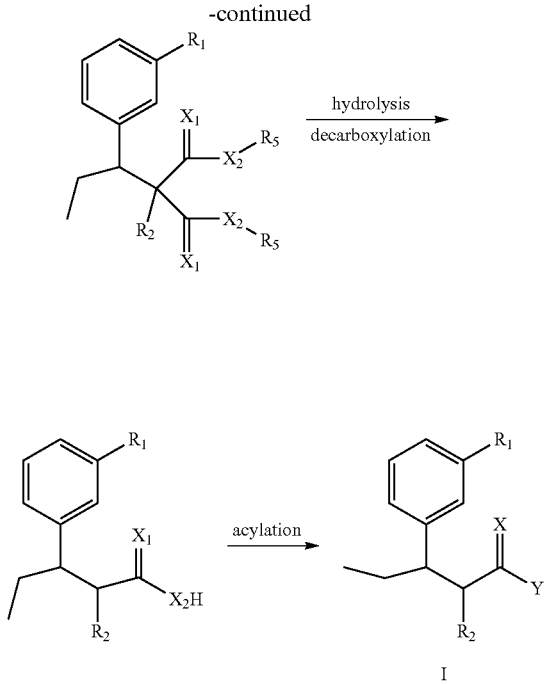

Scheme 1 where the substitution reaction is to react bromide with substituted malonates in a solvent, and is carried out under the condition suitable for catalyzing alkaline compounds;

the hydrolysis decarboxylation reaction is to hydrolyze the relevant substituted malonate into substituted malonic acid in an alkaline aqueous solution to obtain the target compound by high temperature decarboxylation; and the acylation reaction is to react with an acylating reagent, such as thionyl chloride, phosphorus pentachloride and phosphorus tribromide to obtain an acyl halide compound, i.e., compound I.

12

Method 2 is shown as Scheme 2:

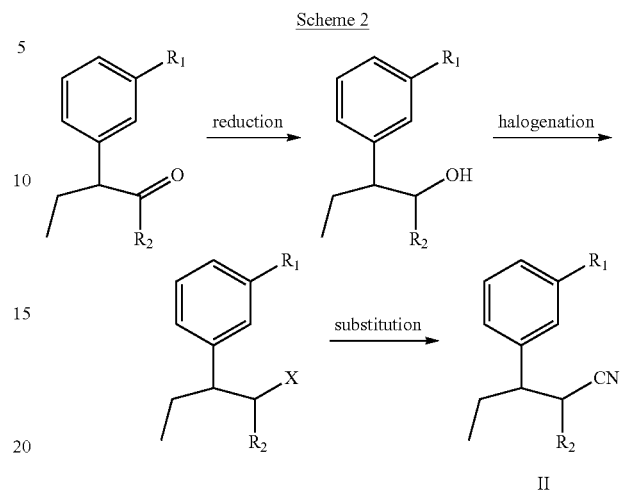

where the reduction reaction is to reduce carbonyl into hydroxyl by a reducer which may be hydrogen, metal oxide, such as sodium borohydride and lithium aluminum hydride;

the halogenation reaction is to substitute hydroxyl with the relevant halogen, and the halogenating reagent may be thionyl chloride, phosphorus pentachloride, phosphorus tribromide or the like; and the substitution reaction is to react a cyanide with the halogenation reaction product to obtain the relevant target compound II, and the cyanide may be sodium cyanide, cuprous cyanide or the like.

In the reaction route above, $R_1$, $R_2$, X and Y are defined as above; $X_1$ and $X_2$ are selected from oxygen or sulfur, and they may be same or not; $R_5$ is selected from hydrogen, substituted or unsubstituted alkyl, substituted or unsubstituted cycloalkyl, substituted or unsubstituted aryl, substituted or unsubstituted aralkyl, substituted or unsubstituted heteroaryl, and substituted or unsubstituted heteroaralkyl.

The method for the preparing tapentadol by using the compound in the invention as the intermediate is as follows:

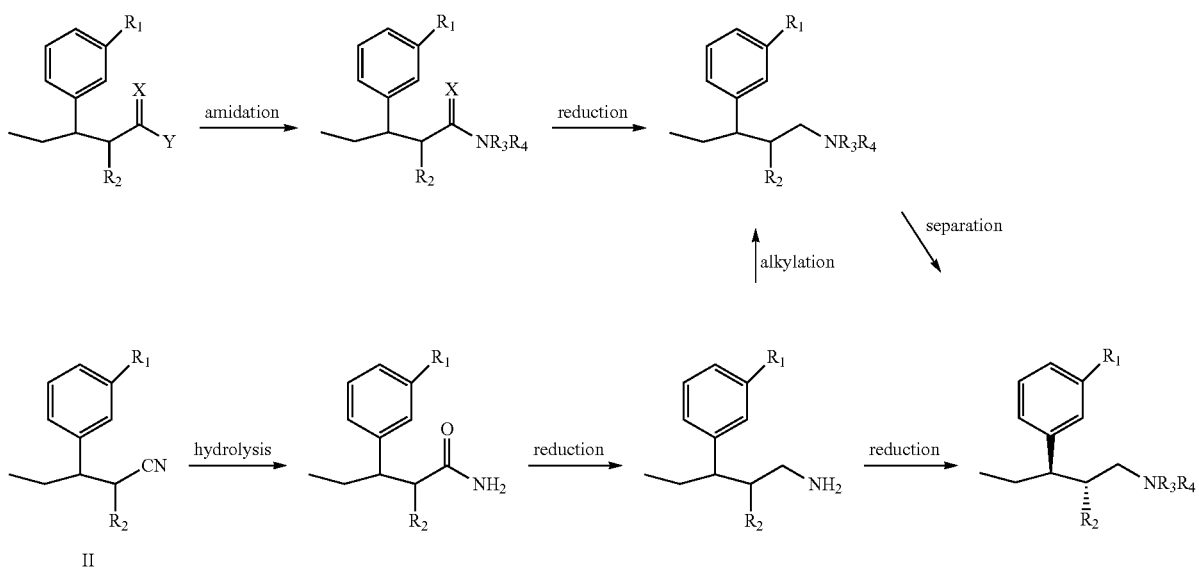

where the amidation reaction is to react compound I with the relevant amide to obtain the relevant amide compound;

the reduction reaction is to reduce the amide into the relevant amine compound by using a proper reducer which usually is hydrogen, borane, sodium borohydride, lithium aluminum hydrid or the like;

the hydrolysis reaction is to hydrolyze the relevant cyanide in an aqueous solution with a certain pH to obtain the relevant amide compound;

the alkylation reaction is to alkylate N on the primary amine by a relevant alkylating reagent which may be haloalkane, such as chloromethane, chloroethane, bromomethane, bromoethane and iodomethane, an ester compound, such as dimethyl sulfate, diethyl sulfate, trimethyl phosphate and methyl p-toluenesulfonate, aldehyde or ketone of various aliphatics or aromatics, or the like; and the separation step is to separate the prepared racemic compound into a single chiral compound by a relevant chiral separator which is an acidic chiral separator, and through the HPLC detection, the content of the chiral compound is 99.56%, and ee %>99.5%.

In the reaction route above, $R_1$, $R_2$, $R_3$, $R_4$, X and Y are defined as above; and preferably, $R_1$ is hydroxyl, $R_2$, $R_3$ and $R_4$ are methyl, and the product is tapentadol.

DETAILED DESCRIPTION OF THE EMBODIMENTS

The embodiments below explain the invention more specifically. However, it should be construed that such embodiments are only for explaining the invention by examples, instead of limiting the scope of the invention in any forms.

Embodiment 1 Preparation of diethyl 2-(3-methoxphenyl)propylmalonate

The steps are: add diethyl methylmalonate and anhydrous DMF into a reaction flask, stir well, T=40, add NaH, after 1-hour consecutive reaction dip the DMF solution of 3-(1-bromopropyl)anisole while stirring, stir at 85 for 18 hours, track that the reaction is substantially completed by TLC (developer: petroleum ether/ethyl acetate (8:1)), pour the reaction product in the water, perform extraction by ethyl acetate until the water layer is not fluorescent, wash the organic layer twice by water without drying to obtain a yellow oily product after decompression and concentration, i.e., diethyl 2-(3-methoxphenyl)propylmalonate.

Molecular formula: $C_{18}H_{26}O_5$, molecular weight: 322.4, MS(m/z): 322.

Elementary analysis: theoretical values: C: 67.06%, H: 8.13%; measured values: C: 67.16%, H: 8.19%.

Embodiment 2 Preparation of 2-methyl-3-(3-methoxyphenyl)valeric acid

The steps are: add diethyl 2-(3-methoxphenyl)propylmalonate, ethanol and water into a reaction flask, adjust the pH value to 14 by sodium hydroxide after stirring them well, perform heating reflux reaction, track the reaction by TLC, keep the pH value of the solution at 14, (developer: petroleum ether/ethyl acetate (4:1)), distil ethanol by decompression, and perform extraction twice by ethyl acetate to separate an organic layer out; adjust the pH value of the water layer to 2 to 3 by an acid, perform extraction by ethyl acetate, separate organic layers out, combine the organic layers, and perform drying by anhydrous magnesium sulphate to obtain a yellow oily product after decompression and concentration; add the yellow oily production in a three-neck flask, reflux and heat it in an oil bath of 15 for 5 hours, pour the resultant into the sodium hydroxide solution to make the pH become alkaline, and exact the undissolved substance by ethyl acetate; and adjust the pH of the water layer to 3 by hydrochloric acid, perform extraction by ethyl acetate, and distil a solvent out after drying and decompression to obtain a yellow liquid, i.e., 2-methyl-3-(3-methoxyphenyl) valeric acid.

Molecular formula: $C_{13}H_{18}O_3$, molecular weight: 222.3, MS(m/z): 223 ($M^+$+H).

Elementary analysis: theoretical values: C: 70.24%, H: 8.16%; measured values: C: 70.32%, H: 8.09%.

$^1$H-NMR (CDCl$_3$, 500 MHz):

δ: 7.09 (t, J=8.5 Hz, 1H, Ar—H), 6.77 (d, J=8.5 Hz, 2H, Ar—H), 6.77 (d, J=8.5 Hz, 1H, Ar—H), 3.90 (s, 3H, —OCH$_3$), 3.10 (m, 1H, Ar—CH), 2.90 (m, 1H, Ar—CH—CH—COOH), 1.62 (m, 2H), 1.19 (d, J=6.5 Hz, 3H), 0.73 (d, J=6.0 Hz, 3H); $^{13}$C-NMR (CDCl$_3$, 125 MHz) δ: 176.0, 160.1, 139.6, 127.3, 123.1, 116.3, 113.1, 60.3, 56.8, 55.8, 44.5, 26.5, 14.3, 11.2.

Embodiment 3 Preparation of 2-methyl-3-(3-hydroxyphenyl)valeric acid

The steps are: add 2-methyl-3-(3-methoxyphenyl) valeric acid into a reaction flask, add hydroiodic acid, and perform heating and reflux for 12 hours; detect the reaction process by TLC; after that, cool the resultant to the room temperature, pour it into an alkaline solution to make the pH become 9, perform extraction by ethyl acetate, reversely adjust the pH of the water layer to about 3.0 after the water layer is separated out, and add ethyl acetate for extraction; and dry the ethyl acetate extracting solution by anhydrous magnesium sulphate, and recycle the solvent by decompression to obtain a light yellow liquid, 2-methyl-3-(3-hydroxyphenyl) valeric acid.

Molecular formula: $C_{18}H_{26}O_5$, molecular weight: 208.3, MS(m/z): 209 ($M^+$+H).

Elementary analysis: theoretical values: C: 69.21%, H: 7.74%; measured values: C: 65.35%, H: 7.56%.

Embodiment 4 Preparation of valeryl 2-methyl-3-(3-methoxyphenyl)chloride (compound 1)

The steps are: add 2-methyl-3-(3-hydroxyphenyl) valeric acid into a three-neck flask, add thionyl chloride, perform reflux for 4 hours, detect that the reaction is substantially completed by TLC, (developer: petroleum ether/ethyl acetate (4:1)); and distil a solvent by decompression to obtain valeryl 2-methyl-3-(3-methoxyphenyl) chloride (Compound 1).

Molecular formula: $C_{13}H_{17}ClO_2$, molecular weight: 240.7, MS(m/z): 240 ($M^+$).

Elementary analysis: theoretical values: C: 64.86%, H: 7.12%; measured values: C: 65.02%, H: 7.24%.

Embodiment 5 Preparation of methyl 2-methyl-3-(3-methoxyphenyl)valerate (Compound 2)

The steps are: add compound 1 and methanol into a three-neck flask, perform reflux for 5 hours, detect that the reaction is substantially completed by TLC, distil a solvent by decompression to obtain a light yellow oily product, valeryl 2-methyl-3-(3-methoxyphenyl)chloride (compound 2).

Molecular formula: $C_{14}H_{20}O_3$, molecular weight: 236.3, MS(m/z): 236 ($M^+$).

Elementary analysis: theoretical values: C: 71.16%, H: 8.53%; measured values: C: 71.09%, H: 8.39%.

Embodiment 6 Preparation of N,N-dimethyl-2-methyl-3-(3-methoxyphenyl)valeramide (Compound 7)

The step are: add the aqueous solution of dimethylamine (33%) into a three-neck flask, T=10, dip compound 1 and NaOH to make pH=12 to 14; after that, keep performing the reaction at the room temperature for 2 hours; perform extraction twice by ethyl acetate, prepare the organic phase, rinse twice by 10% hydrochloric acid, and perform drying by anhydrous magnesium sulfate; recycle the solvent by decompression to obtain a light yellow oily product which is dissolved by isopropanol; and add a seed crystal to obtain a white solid, N,N-dimethyl-2-methyl-3-(3-methoxyphenyl) valeramide (compound 7).

Molecular formula: $C_{15}H_{23}NO_2$, molecular weight: 249.4, MS(m/z): 249 (M$^+$).

Elementary analysis: theoretical values: C: 72.25%, H: 9.30%, N: 5.62%; measured values: C: 72.31%, H: 9.35%, N: 5.73%.

Embodiment 7 Preparation of N,N-dimethyl-2-methyl-3-(3-hydroxyphenyl)valeramide (Compound 9)

The steps are: add compound 7 into a reaction flask, add hydroiodic acid, perform heating and reflux for 5 hours; detect the reaction process by TLC; after that, cool the resultant to the room temperature, pour it to an alkaline solution to make the pH become 9, and perform extraction by ethyl acetate and rinse by water; and recycle the solvent after drying and decompression to obtain a light yellow liquid, N,N-dimethyl-2-methyl-3-(3-hydroxyphenyl) valeramide (compound 9).

Molecular formula: $C_{14}H_{21}NO_2$, molecular weight: 235.3, MS(m/z): 235 (M$^+$).

Elementary analysis: theoretical values: C: 71.46%, H: 8.99%, N: 5.95%; measured values: C: 71.33%, H: 9.05%, N: 5.92%.

$^1$H-NMR (CDCl$_3$, 500 MHz) δ: 7.11 (t, J=8.0 Hz, 1H, Ar—H), 6.74 (d, J=8.0 Hz, 2H, Ar—H), 6.62 (d, J=8.0 Hz, 1H, Ar—H), 3.03 (m, 2H, Ar—CH, Ar—CH—CH—COOH), 2.86 (s, 6H, N(CH$_3$)$_2$), 1.66 (m, 2H), 1.12(d, J=6.5 Hz, 3H), 0.75 (d, J=6.0 Hz, 3H); $^{13}$C-NMR (CDCl$_3$, 125 MHz) δ: 176.0, 158.3, 140.6, 129.3, 121.8, 114.9, 113.6, 59.2, 42.7, 39.4, 26.5, 15.2, 11.1.

Embodiment 8 Preparation of N,N-diethyl-2-methyl-3-(3-methoxyphenyl)valeramide (Compound 11)

Compound 11 can be obtained by replacing dimethylamine in Embodiment 6 with diethylamine.

Molecular formula: $C_{17}H_{27}NO_2$, molecular weight: 277.4, MS(m/z): 277 (M$^+$).

Elementary analysis: theoretical values: C: 73.61%, H: 9.81%, N: 5.05%; measured values: C: 73.43%, H: 9.75%, N: 5.09%.

Embodiment 9 Preparation of N,N-dipropyl-2-methyl-3-(3-methoxyphenyl)valeramide (Compound 12)

Compound 12 can be obtained according to the operation of the method by replacing dimethylamine in Embodiment 6 with dipropylamine.

Molecular formula: $C_{19}H_{31}NO_2$, molecular weight: 305.5, MS(m/z): 305 (M$^+$).

Elementary analysis: theoretical values: C: 74.71%, H: 10.23%, N: 4.59%; measured values: C: 74.68%, H: 10.21%, N: 4.61%.

Embodiment 10 Preparation of N,N-diisopropyl-2-methyl-3-(3-methoxyphenyl)valeramide (Compound 13)

Compound 13 can be obtained according to the operation of the method by replacing dimethylamine in Embodiment 6 with diisopropylamine.

Molecular formula: $C_{19}H_{31}NO_2$, molecular weight: 305.5, MS(m/z): 305 (M$^+$).

Elementary analysis: theoretical values: C: 74.71%, H: 10.23%, N: 4.59%; measured values: C: 74.74%, H: 10.30%, N: 4.56%.

Embodiment 11 Preparation of 3-(3-methoxyphenyl)-2-methyl-1-(piperidin-1-yl)pentan-1-one (Compound 14)

Compound 14 can be obtained according to the operation of the method by replacing dimethylamine in Embodiment 6 with piperidine.

Molecular formula: $C_{18}H_{27}NO_2$, molecular weight: 289.4, MS(m/z): 289 (M$^+$).

Elementary analysis: theoretical values: C: 74.70%, H: 9.40%, N: 4.84%; measured values: C: 74.79%, H: 9.35%, N: 4.77%.

Embodiment 12 Preparation of 3-(3-methoxyphenyl)-2-methyl-1-(4-methylpiperidin-1-yl)pentan-1-one (Compound 15)

Compound 15 can be obtained according to the operation of the method by replacing dimethylamine in Embodiment 6 with 4-methylpiperidine.

Molecular formula: $C_{19}H_{29}NO_2$, molecular weight: 303.45, MS(m/z): 304 (M$^+$+1).

Elementary analysis: theoretical values: C: 75.21%, H: 9.63%, N: 4.62%; measured values: C: 75.19%, H: 9.57%, N: 4.76%.

Embodiment 13 Preparation of 3-(3-methoxyphenyl)-2-methyl-1-(morpholin-1-yl)pentan-1-one (Compound 16)

Compound 16 can be obtained according to the operation of the method by replacing dimethylamine in Embodiment 6 with morpholine.

Molecular formula: $C_{17}H_{25}NO3$, molecular weight: 291.39, MS(m/z): 291 (M$^+$).

Elementary analysis: theoretical values: C: 70.07%, H: 8.65%, N: 4.81%; measured values: C: 70.11%, H: 8.57%, N: 4.79%.

Embodiment 14 Preparation of 3-(3-methoxyphenyl)-2-methyl-1-(pyrrolidin-1-yl)pentan-1-one (compound 17)

Compound 17 can be obtained according to the operation of the method by replacing dimethylamine in Embodiment 6 with pyrrolidine.

Molecular formula: $C_{17}H_{25}NO_2$, molecular weight: 275.39, MS(m/z): 275 (M$^+$).

Elementary analysis: theoretical values: C: 74.14%, H: 9.15%, N: 5.09%; measured values: C: 74.12%, H: 9.17%, N: 4.98%.

Embodiment 15 Preparation of N,N-dimethyl-2-methyl-3-(3-chlorophenyl)valeramide (Compound 18)

Compound 18 can be obtained according to the operation of the method by replacing 3-(1-bromopropyl) anisole in Embodiment 1 with 3-(1-bromopropyl)chlorobenzene.

Molecular formula: $C_{14}H_{20}ClNO$, molecular weight: 253.77, MS(m/z): 253 ($M^+$).

Elementary analysis: theoretical values: C: 66.26%, H: 7.94%, N: 5.52%; measured values: C: 66.32%, H: 8.05%, N: 5.56%.

Embodiment 16 Preparation of N,N-diethyl-3-(3-chlorophenyl)-2-methyl valeramide (Compound 19)

Compound 19 can be obtained according to the operation of the method by replacing dimethylamine in Embodiment 12 with diethylamine.

Molecular formula: $C_{16}H_{24}ClNO$, molecular weight: 281.83, MS(m/z): 281 ($M^+$).

Elementary analysis: theoretical values: C: 68.19%, H: 8.58%, N: 4.97%; measured values: C: 68.22%, H: 8.65%, N: 4.86%.

Embodiment 17 Preparation of 3-(3-chlorophenyl)-2-methyl-N,N-dipropyl valeramide (Compound 20)

Compound 20 can be obtained according to the operation of the method by replacing dimethylamine in Embodiment 12 with dipropylamine.

Molecular formula: $C_{18}H_{28}ClNO$, molecular weight: 309.88, MS(m/z): 309 ($M^+$).

Elementary analysis: theoretical values: C: 69.77%, H: 9.11%, N: 4.52%; measured values: C: 69.83%, H: 9.21%, N: 4.56%.

Embodiment 18 Preparation of 3-(3-chlorophenyl)-2-methyl-N,N-isopropyl valeramide (Compound 21)

Compound 21 can be obtained according to the operation of the method by replacing dimethylamine in Embodiment 12 with isopropylamine.

Molecular formula: $C_{17}H_{24}ClNO$, molecular weight: 293.84, MS(m/z): 294 ($M^+$).

Elementary analysis: theoretical values: C: 69.77%, H: 9.11%, N: 4.52%; measured values: C: 69.84%, H: 9.23%, N: 4.59%.

Embodiment 19 Preparation of 3-(3-chlorophenyl)-2-methyl-1-(piperidin-1-yl)pentan-1-one (Compound 22)

Compound 22 can be obtained according to the operation of the method by replacing dimethylamine in Embodiment 12 with piperidine.

Molecular formula: $C_{17}H_{24}ClNO$, molecular weight: 293.84, MS(m/z): 294 ($M^+$).

Elementary analysis: theoretical values: C: 69.49%, H: 8.23%, N: 12.07%; measured values: C: 69.44%, H: 8.31%, N: 4.75%.

Embodiment 20 Preparation of 3-(3-chlorophenyl)-2-methyl-1-(4-methylpiperidin-1-yl)pentan-1-one (Compound 23)

Compound 23 can be obtained according to the operation of the method by replacing dimethylamine in Embodiment 12 with 4-methylpiperidine.

Molecular formula: $C_{18}H_{26}ClNO$, molecular weight: 307.87, MS(m/z): 307 ($M^+$).

Elementary analysis: theoretical values: C: 70.23%, H: 8.51%, N: 4.55%; measured values: C: 70.22%, H: 8.65%, N: 4.62%.

Embodiment 21 Preparation of 3-(3-chlorophenyl)-2-methyl-1-(morpholin-1-yl)pentan-1-one (Compound 24)

Compound 24 can be obtained according to the operation of the method by replacing dimethylamine in Embodiment 12 with morpholine.

Molecular formula: $C_{18}H_{26}ClNO$, molecular weight: 307.87, MS(m/z): 307 ($M^+$).

Elementary analysis: theoretical values: C: 64.97%, H: 7.50%, N: 4.73%; measured values: C: 65.02%, H: 7.55%, N: 4.68%.

Embodiment 22 Preparation of 3-(3-chlorophenyl)-2-methyl-1-(pyrrolidin-1-yl)pentan-1-one (Compound 25)

Compound 25 can be obtained according to the operation of the method by replacing dimethylamine in Embodiment 12 with pyrrolidine.

Molecular formula: $C_{16}H_{22}ClNO$, molecular weight: 279.81, MS(m/z): 279 ($M^+$).

Elementary analysis: theoretical values: C: 68.68%, H: 7.93%, N: 5.01%; measured values: C: 68.70%, H: 7.02%, N: 5.12%.

Embodiment 23 Preparation of 3-(3-methoxy-phenyl)-N,N,2-trimethyl pentylamine The steps are: add anhydrous ether into a reaction flask, and add lithium aluminum hydride under the condition of ice bath; dip compound 7, control the temperature within 10, after the dipping detect the reaction process by TLC; after the reaction is ended, pour the reaction liquid in the ice water slowly, separate the ether layer out, rinse by water, perform drying, and recycle the solvent by decompression to obtain a light yellow liquid, 3-(3-methoxy-phenyl)-N,N,2-trimethyl pentylamine. Yield: 85%.

Molecular formula: $C_{15}H_{25}NO$, molecular weight: 235.4, MS(m/z): 235 ($M^+$).

Embodiment 24 Preparation of 3-(3-hydroxy-phenyl)-N,N,2-trimethyl pentylamine The steps are: add 3-(3-methoxy-phenyl)-N,N,2-trimethyl pentylamine into a reaction flask, add hydroiodic acid, and perform heating and reflux for 5 hours; detect the reaction process by TLC; after that, cool the resultant to the room temperature, pour it to an alkaline solution to make the pH become 9, perform extraction by ethyl acetate and rinse by water; recycle the solvent by drying and decompression to obtain a light yellow liquid, 3-(3-hydroxy-phenyl)-N,N,2-trimethyl pentylamine; and separate the mother solution by a separator, form the salt by the acidification of hydrochloric acid to obtain tapentadol hydrochloride. HPLC: 99.56%, ee %>99.5%.

Molecular formula: $C_{14}H_{23}NO \cdot HCl$, molecular weight: 257.8, MS(m/z): 221 ($M^+$−HCl).

Elementary analysis: theoretical values: C: 65.23%, H: 9.38%, N: 5.43%; measured values: C: 65.31%, H: 9.35%, N: 5.31%.

$^1$H-NMR (D$_2$O, 500 MHz) δ: 7.15 (t, J=8.0 Hz, 1H, Ar—H), 6.69(dd,J=8.0 Hz,2H,Ar—H), 6.65(d,J=8.0 Hz,1H, Ar—H), 2.71 (m, 2H, —CH$_2$), 2.62(s, 6H, N(CH$_3$)$_2$), 2.20 (m,1H,—CH—CH$_3$),2.04(m,1H,—CH),1.73,1.42(m,2H,—CH$_2$CH$_3$),0.96(d,3H, —CHCH$_3$),0.54(t,3H,—CH$_2$CH$_3$).

Embodiment 25 Preparation of 3-(3-methoxy-phenyl)-2-methyl-N,N-diethyl pentylamine 3-(3-methoxy-phenyl)-2-methyl-N,N-diethyl pentylamine can be obtained by compound 11 according to Embodiment 23.

Molecular formula: $C_{17}H_{29}NO$, molecular weight: 263.4, MS(m/z): 264 ($M^+$+H).

Elementary analysis: theoretical values: C: 77.51%, H: 11.09%, N: 5.31%; measured values: C: 77.39%, H: 11.15%, N: 5.42%.

Embodiment 26 Preparation of (1R,2R)-3-(3-diethylamine-1-ethyl-2-methylpropyl)-phenol hydrochloride (1R,2R)-3-(3-diethylamine-1-ethyl-2-methylpropyl)-phenol hydrochloride can be obtained by 3-(3-methoxy-phenyl)-2-methyl-N,N-diethyl pentylamine according to Embodiment 24.

Molecular formula: $C_{16}H_{27}NO \cdot HCl$, molecular weight: 285.8, MS(m/z): 249 ($M^+$−HCl).

Elementary analysis: theoretical values: C: 71.21%, H: 10.46%, N: 5.19%; measured values: C: 71.11%, H: 10.35%, N: 5.21%.

Embodiment 27 Preparation of 3-(3-methoxy-phenyl)-2-methyl-N,N-dipropyl pentylamine 3-(3-methoxy-phenyl)-2-methyl-N,N-dipropyl pentylamine can be obtained by compound 12 according to Embodiment 23.

Molecular formula: $C_{19}H_{33}NO$, molecular weight: 291.5, MS(m/z): 290 ($M^+$−H).

Elementary analysis: theoretical values: C: 78.29%, H: 11.41%, N: 4.81%; measured values: C: 78.33%, H: 11.52%, N: 4.76%.

Embodiment 28 Preparation of (1R,2R)-3-(3-dipropylamine-1-ethyl-2-methylpropyl)-phenol hydrochloride (1R,2R)-3-(3-dipropylamine-1-ethyl-2-methylpropyl)-phenol hydrochloride can be obtained by 3-(3-methoxy-phenyl)-2-methyl-N,N-dipropyl pentylamine according to Embodiment 24.

Molecular formula: $C_{18}H_{31}NO \cdot HCl$, molecular weight: 313.9, MS(m/z): 277 ($M^+$−HCl).

Elementary analysis: theoretical values: C: 68.87%, H: 10.28%, N: 4.46%; measured values: C: 68.74%, H: 10.33%, N: 4.36%.

Embodiment 29 Preparation of 3-(3-methoxy-phenyl)-2-methyl-N,N-diisopropyl pentylamine 3-(3-methoxy-phenyl)-2-methyl-N,N-isopropyl pentylamine can be obtained by compound 13 according to Embodiment 23.

Molecular formula: $C_{19}H_{33}NO$, molecular weight: 291.5, MS(m/z): 290 ($M^+$−H).

Elementary analysis: theoretical values: C: 78.29%, H: 11.41%, N: 4.81%; measured values: C: 78.33%, H: 11.52%, N: 4.76%.

Embodiment 30 Preparation of (1R,2R)-3-(3-diisopropylamine-1-ethyl-2-methylpropyl)-phenol hydrochloride (1R,2R)-3-(3-isopropylamine-1-ethyl-2-methylpropyl)-phenol hydrochloride can be obtained by 3-(3-methoxy-phenyl)-2-methyl-N,N-dipropyl pentylamine according to Embodiment 24.

Molecular formula: $C_{18}H_{31}NO \cdot HCl$, molecular weight: 313.9, MS(m/z): 277 ($M^+$−HCl).

Elementary analysis: theoretical values: C: 68.87%, H: 10.28%, N: 4.46%; measured values: C: 68.74%, H: 10.33%, N: 4.36%.

Embodiment 31 Preparation of 1-[3-(3-methoxyphenyl)-2-methyl-pentalkyl]-piperidine 1-[3-(3-methoxyphenyl)-2-methyl-pentalkyl]-piperidine can be obtained by compound 14 according to Embodiment 23.

Molecular formula: $C_{18}H_{29}NO$, molecular weight: 275.4, MS(m/z): 275 ($M^+$).

Elementary analysis: theoretical values: C: 78.49%, H: 10.61%, N: 5.09%; measured values: C: 78.42%, H: 10.55%, N: 5.21%.

Embodiment 32 Preparation of (1R,2R)-3-(1-ethyl-2-methyl-3-piperidin-1-yl-propyl)-phenol hydrochloride (1R,2R)-3-(1-ethyl-2-methyl-3-piperidin-1-yl-propyl)-phenol hydrochloride can be obtained by 1-[3-(3-methoxyphenyl)-2-methyl-pentalkyl]-piperidine according to Embodiment 24.

Molecular formula: $C_{17}H_{27}NO \cdot HCl$, molecular weight: 297.9, MS(m/z): 261 ($M^+$−HCl).

Elementary analysis: theoretical values: C: 72.44%, H: 10.01%, N: 4.97%; measured values: C: 72.36%, H: 10.15%, N: 5.02%.

Embodiment 33 Preparation of 1-[3-(3-methoxyphenyl)-2-methyl-pentalkyl]-4-methyl-piperidine 1-[3-(3-methoxyphenyl)-2-methyl-pentalkyl]-4-methyl-piperidine can be obtained by compound 15 according to Embodiment 23.

Molecular formula: $C_{19}H_{33}NO$, molecular weight: 291.5, MS(m/z): 291 ($M^+$).

Elementary analysis: theoretical values: C: 78.29%, H: 11.41%, N: 4.80%; measured values: C: 78.31%, H: 11.35%, N: 4.82%.

Embodiment 34 Preparation of (1R,2R)-3-[1-ethyl-2-methyl-3-(4-methyl-piperidin-1-yl)-propyl]-phenol hydrochloride (1R,2R)-3-[1-ethyl-2-methyl-3-(4-methyl-piperidin-1-yl)-propyl]-phenol hydrochloride can be obtained by 1-[3-(3-methoxyphenyl)-2-methyl-pentalkyl]-4-methyl-piperidine according to Embodiment 24.

Molecular formula: $C_{18}H_{29}NO \cdot HCl$, molecular weight: 311.89, MS(m/z): 275 ($M^+-HCl$).

Elementary analysis: theoretical values: C: 69.31%, H: 9.70%, N: 4.49%; measured values: C: 69.42%, H: 9.72%, N: 4.46%.

Embodiment 35 Preparation of 4-[3-(3-methoxyphenyl)-2-methyl-pentalkyl]-morpholine 4-[3-(3-methoxyphenyl)-2-methyl-pentalkyl]-morpholine can be obtained by compound 16 according to Embodiment 23.

Molecular formula: $C_{17}H_{27}NO_2$, molecular weight: 277.4, MS(m/z): 277 ($M^+$).

Elementary analysis: theoretical values: C: 73.60%, H: 9.81%, N: 5.05%; measured values: C: 73.71%, H: 9.85%, N: 5.01%.

Embodiment 36 Preparation of (1R,2R)-3-(1-ethyl-2-methyl-4-morpholin-4-yl-propyl)-phenol hydrochloride (1R,2R)-3-(1-ethyl-2-methyl-3-morpholin-4-yl-propyl)-phenol hydrochloride can be obtained by 4-[3-(3-methoxyphenyl)-2-methyl-pentalkyl]-morpholine according to Embodiment 24.

Molecular formula: $C_{16}H_{27}NO_2 \cdot HCl$, molecular weight: 299.8, MS(m/z): 263 ($M^+-HCl$).

Elementary analysis: theoretical values: C: 64.09%, H: 8.74%, N: 4.67%; measured values: C: 64.12%, H: 9.79%, N: 4.71%.

Embodiment 35 Preparation of 1-[3-(3-methoxyphenyl)-2-methyl-pentalkyl]-pyrrolidine 1-[3-(3-methoxyphenyl)-2-methyl-pentalkyl]-pyrrolidine can be obtained by compound 17 according to Embodiment 23.

Molecular formula: $C_{17}H_{27}NO$, molecular weight: 261.4, MS(m/z): 261 ($M^+$).

Elementary analysis: theoretical values: C: 78.11%, H: 10.41%, N: 5.35%; measured values: C: 78.24%, H: 10.35%, N: 5.29%.

Embodiment 36 Preparation of (1R,2R)-3-(1-ethyl-2-methyl-3-pyrrolidin-4-yl-propyl)-phenol hydrochloride (1R,2R)-3-(1-ethyl-2-methyl-3-pyrrolidin-1-yl-propyl)-phenol hydrochloride can be obtained by 1-[3-(3-methoxyphenyl)-2-methyl-pentalkyl]-pyrrolidine according to Embodiment 24.

Molecular formula: $C_{14}H_{23}NO \cdot HCl$, molecular weight: 283.8, MS(m/z): 247 ($M^+-HCl$).

Elementary analysis: theoretical values: C: 67.70%, H: 9.23%, N: 5.64%; measured values: C: 67.76%, H: 9.31%, N: 5.59%.

Embodiment 37 Preparation of 3-(3-methoxyphenyl)-2-pentanol

The steps are: under the condition of ice bath, add methanol and 3-(3-methoxyphenyl)-2-pentanol into a reaction flask, stir, introduce $N_2$, after the system is reduced about 0 add 96% sodium borohydride for four times, keep performing the reaction at the temperature for 30 minutes, track that the reaction is substantially completed by TLC, distil the solvent by decompression, pour the reaction product in the water, and perform extraction by ethyl acetate and drying by anhydrous magnesium sulfate to obtain 3-(3-methoxyphenyl)-2-pentanol after decompression and concentration, yield: 99%.

Molecular formula: $C_{12}H_{18}O_2$, molecular weight: 194.3, MS(m/z): 195 ($M^++H$).

Elementary analysis: theoretical values: C: 74.19%, H: 9.34%; measured values: C: 74.22%, H: 9.32%.

Embodiment 38 Preparation of 1-(2-bromopentane)-3-methoxybenzene

The steps are: under the protection of $N_2$, add 3-(3-methoxyphenyl)-2-pentanol and dichloromethane into a reaction flask, lower the temperature to about −5 by ice bath, dip $PBr_3$, keep the temperature, stir at the temperature for 1 hour, track that the reaction is substantially completed by TLC, pour the reaction product in the ice water, perform extraction by dichloromethane, rinse the organic layer by the aqueous solution of sodium bicarbonate and then by water, and perform drying by anhydrous magnesium sulfate to obtain 1-(2-bromopentane)-3-methoxybenzene after decompression and concentration, yield: 95%.

Molecular formula: $C_{12}H_{17}BrO$, molecular weight: 256.2, MS(m/z): 257 ($M^++H$).

Elementary analysis: theoretical values: C: 56.04%, H: 6.66%; measured values: C: 56.11%, H: 6.62%.

Embodiment 39 Preparation of 2-methyl-3-(3-methoxyphenyl)pentanenitrile (Compound 43)

The steps are: add sodium cyanide and DMF into a reaction flask, rise the temperature to 85, dip the DMF solution of 1-(2-bromopentane)-3-methoxybenzene, keep the temperature, stir at the temperature for 8 hours, track that the reaction is substantially completed by TLC, and lower the temperature to the room temperature; andpour the reaction liquid in the water, perform extraction by ethyl acetate until the water layer is not fluorescent, and rinse the organic layer twice by water without drying to obtain 2-methyl-3-(3-methoxyphenyl)pentanenitrile after decompression and concentration.

Molecular formula: $C_{13}H_{17}NO$, molecular weight: 203.3, MS(m/z): 204 ($M^++H$).

Elementary analysis: theoretical values: C: 76.81%, H: 8.43%; measured values: C: 76.75%, H: 8.46%.

The invention has been described in connection with the embodiments. It should be construed that the description and embodiments above are only used for explaining the invention by examples. Various replacements and improvements of the invention can be made by those skilled in the art within the spirit and scope of the invention and should be construed to be within the protection scope of the invention

What is claimed is:

1. A method for preparing the compound shown as formula I, characterized in that the reaction route is:

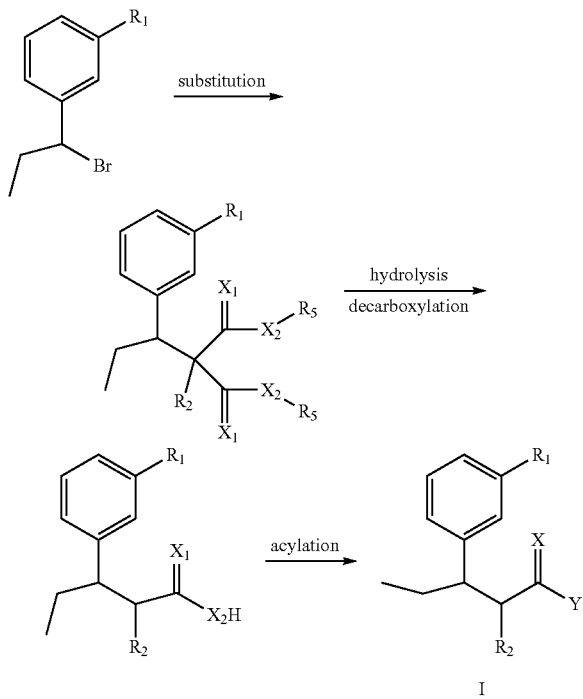

wherein
- $R_1$ is selected from halogen, hydroxy, amino, nitrile, nitro, acyl, substituted or unsubstituted alkyl, substituted or unsubstituted cycloalkyl, substituted or unsubstituted alkoxyl, substituted or unsubstituted aryl, substituted or unsubstituted aralkyl, substituted or unsubstituted heteroaryl, substituted or unsubstituted heteroaralkyl, acyloxy, oxyacyl and sulfonyl;
- $R_2$ is selected from substituted or unsubstituted alkyl, substituted or unsubstituted cycloalkyl, substituted or unsubstituted aryl, substituted or unsubstituted aralkyl, substituted or unsubstituted heteroaryl, and substituted or unsubstituted heteroaralkyl;
- X is selected from oxygen or sulfur;
- Y is selected from halogen, $OR_2$ or $NR_3R_4$;
- $R_3$ and $R_4$ are separately hydrogen, substituted or unsubstituted alkyl, substituted or unsubstituted cycloalkyl, substituted or unsubstituted aryl, substituted or unsubstituted aralkyl, substituted or unsubstituted heteroaryl, and substituted or unsubstituted heteroaralkyl; or $R_3$ $R_4$ and N form saturated or unsaturated heterocyclyl jointly;
- $X_1$ and $X_2$ are selected from oxygen or sulfur, and they can be same or not; and
- $R_5$ is selected from hydrogen, substituted or unsubstituted alkyl, substituted or unsubstituted cycloalkyl, substituted or unsubstituted aryl, substituted or unsubstituted aralkyl, substituted or unsubstituted heteroaryl, and substituted or unsubstituted heteroaralkyl.

2. The method according to claim 1, wherein
$R_1$ is elected from F, Cl, Br, $CHF_2$, $CF_3$, OH, $SO_2CH_3$, $NH_2$, CN, CHO, —$C_{1-6}$ alkyl, —$C_{1\neq}$alkoxyl, —$C_{3-7}$ cycloalkyl, —$C_{1-3}$ alkylenephenyl, —$C_{1-3}$ alkylenenaphthyl, tetrahydrofuran or —C (=O) $C_{1-6}$ alkyl; and Y is selected from $OR_2$, $R_2$ is selected from methyl, ethyl, n-propyl or isopropyl.

3. The method according to claim 2, wherein $R_1$ is selected from Cl, methyl, OH, $NH_2$ or methoxy.

4. The method according to claim 1, wherein Y is selected from $NR_3R_4$, wherein $R_3$, $R_4$ and N form substituted or unsubstituted saturated nitrogen-containing heteorcyclyl containing oxygen or not jointly.

5. The method according to claim 1, wherein $R_3$, $R_4$ and N form tetrahydropyrrole ring, piperidine ring, 4-methylpiperidine ring, morpholine ring, methylpiperazine ring or 4-hydroxypiperidine jointly.

6. The method according to claim 1, wherein compounds of formula I selected from:
- valeryl 2-methyl-3-(3-methoxyphenyl) chloride;
- methyl 2-methyl-3-(3-methoxyphenyl) valerate;
- methyl 2-methyl-3-(3-methoxyphenyl) sulfovalerate;
- methyl 2-methyl-3-(3-hydroxyphenyl) valerate;
- methyl 2-methyl-3-(3-hydroxyphenyl) sulfovalerate;
- 2-methyl-3-(3-hydroxyphenyl) sulfovaleramide;
- N,N-dimethyl-2-methyl-3-(3-methoxyphenyl) valeramide;
- N,N-dimethyl-2-methyl-3-(3-methoxyphenyl) sulfovaleramide;
- N,N-dimethyl-2-methyl-3-(3-hydroxyphenyl) valeramide;
- N,N-dimethyl-2-methyl-3-(3-hydroxyphenyl) sulfovaleramide;
- N,N-diethyl-2-methyl-3-(3-methoxyphenyl) valeramide;
- N,N-dipropyl-2-methyl-3-(3-methoxyphenyl) valeramide;
- N,N-isopropyl-2-methyl-3-(3-methoxyphenyl) valeramide;
- 3-(3-methoxyphenyl)-2-methyl-1-(piperidin-1-yl) pentan-1-one;
- 3-(3-methoxyphenyl)-2-methyl-1-(4-methylpiperidin-1-yl) pentan-1-one;
- 3-(3-methoxyphenyl)-2-methyl-1-(morpholin-1-yl) pentan-1-one;
- 3-(3-methoxyphenyl)-2-methyl-1-(pyrrolidin-1-yl) pentan-1-one;
- N,N-dimethyl-2-methyl-3-(3-chlorophenyl) valeramide;
- N,N-diethyl-2-methyl-3-(3-chlorophenyl) valeramide;
- N,N-dipropyl-2-methyl-3-(3-chlorophenyl) valeramide;
- N,N-isopropyl-2-methyl-3-(3-chlorophenyl) valeramide;
- 3-(3-chlorophenyl)-2-methyl-1-(piperidin-1-yl) pentan-1-one;
- 3-(3-chlorophenyl)-2-methyl-1-(4-methylpiperidin-1-yl) pentan-1-one;
- 3-(3-chlorophenyl)-2-methyl-1-(morpholin-1-yl) pentan-1-one;
- 3-(3-chlorophenyl)-2-methyl-1-(pyrrolidin-1-yl) pentan-1-one;
- N,N-dimethyl-2-methyl-3-(3-methylphenyl) valeramide;
- N,N-diethyl-2-methyl-3-(3-methylphenyl) valeramide;
- N,N-dipropyl-2-methyl-3-(3-methylphenyl) valeramide;
- N,N-isopropyl-2-methyl-3-(3-methylphenyl) valeramide;
- 3-(3-methylphenyl)-2-methyl-1-(piperidin-1-yl) pentan-1-one;
- 3-(3-methylphenyl)-2-methyl-1-(4-methylpiperidin-1-yl) pentan-1-one;
- 3-(3-methylphenyl)-2-methyl-1-(morpholin-1-yl) pentan-1-one;
- 3-(3-methylphenyl)-2-methyl-1-(pyrrolidin-1-yl) pentan-1-one;
- N,N-dimethyl-2-methyl-3-(3-aminophenyl) valeramide;
- N,N-diethyl-2-methyl-3-(3-aminophenyl) valeramide;

N,N-dipropyl-2-methyl-3-(3-aminophenyl) valeramide;
N,N-isopropyl-2-methyl-3-(3-aminophenyl) valeramide;
3-(3-aminophenyl)-2-methyl-1-(piperidin-1-yl) pentan-1-one;
3-(3-aminophenyl)-2-methyl-1-(4-methylpiperidin-1-yl) pentan-1-one;
3-(3-aminophenyl)-2-methyl-1-(morpholin-1-yl) pentan-1-one; and
3-(3-aminophenyl)-2-methyl-1-(pyrrolidin-1-yl) pentan-1-one.

* * * * *